United States Patent [19]

Karnemaat

[11] 3,939,280

[45] Feb. 17, 1976

[54] PROCESS FOR TREATING ANIMAL WASTE

[75] Inventor: John N. Karnemaat, Comstock Township, Kalamazoo County, Mich.

[73] Assignee: General Environmental Systems Co., Inc., Warsaw, Ind.

[22] Filed: Aug. 30, 1974

[21] Appl. No.: 501,888

[52] U.S. Cl. ................................ 426/2; 426/69
[51] Int. Cl.² ........................................ A23K 1/00
[58] Field of Search .......... 426/2, 69, 807, 641, 54, 426/323

[56] References Cited

UNITED STATES PATENTS

| | | | |
|---|---|---|---|
| 2,687,354 | 7/1954 | Gribbins | 426/69 |
| 3,729,320 | 4/1973 | Kramer | 426/2 |

Primary Examiner—A. Louis Monacell
Assistant Examiner—R. B. Penland
Attorney, Agent, or Firm—Woodhams, Blanchard and Flynn

[57] ABSTRACT

A process of treating poultry manure with acid, formaldehyde and urea to obtain a pathogen-free product suitable as a feedstuff for ruminant animals.

13 Claims, No Drawings

PROCESS FOR TREATING ANIMAL WASTE

BACKGROUND OF THE INVENTION

1. Field of the Invention

This invention relates to a process for transforming poultry manure into a material possessing improved properties for use as an ingredient in feed rations for animals.

2. Description of the Prior Art

Poultry manure has been utilized for centuries as a soil enriching material because it contains an advantageous mixture of organic protein, inorganic nitrogen, fiber and minerals. On small farms it is frequently mixed with straw and other litter for use as a soil conditioner.

In large poultry raising operations involving many thousands of caged birds (layers and/or broilers), the freshly voided poultry excreta passes through the wire mesh bottom walls of the poultry cages, and accumulates substantially uncontaminated on the floor, or it is collected in pits designed for this purpose. The excreta can be easily collected, and it is essentially free of other materials, except for feathers.

The disposal of this material, which is collected in large quantities, poses a serious problem to the poultry industry. It is customary to remove the accumulated poultry manure periodically from under the cages and transport it to a disposal area some distance away. After drying and composting the poultry manure for a period of days or weeks, it is then used as a landfill, or it is sold as a soil builder. A major use of poultry manure at the present time is as a soil enriching agent, based on its inherent phosphorus content of 1 to 2 percent and nitrogen content of 3 to 4 percent. None of these uses, however, recover the full potential economic value of poultry manure.

Poultry excreta has a pH of about 6.0 to 7.0 when voided, and it contains from about 70 to 85 percent moisture. It is reported that chicken manure, on an air dry weight basis (about 11 percent moisture), has the following analysis as regards nitrogenous substances:

| | Range wt.% | Mean wt.% |
|---|---|---|
| Total protein equivalent (N + 6.25%) (true protein plus non-protein nitrogen calculated as protein equivalent) | 15.2–36.8 | 28.7 |
| True protein | 8.1–12.9 | 10.5 |

Under present methods of handling poultry manure, within about 24 to 48 hours after excretion, the action of the bacterial flora and the unstable ammoniacal compounds present therein, coupled with the high moisture content, cause the pH to rise to somewhat above 7.0, usually to at least about 8.0 to 9.0. Additional protein breakdown with concomitant release of ammonia occurs, causing the temperature of the manure pile to rise, thereby resulting in an undesirable further protein breakdown.

Over the past several years poultry manure has attracted a considerable amount of interest because of its relatively high protein content. This interest has recently further increased greatly due to the worldwide shortage of protein. State and federal regulatory agencies are presently in the process of establishing regulations regarding the utilization of poultry manure as a supplemental feed ingredient in feed rations for animals, particularly ruminant farm animals such as cattle. The standards being established by the regulations are concerned with, for example, uniformity of product, freedom from toxic levels of materials such as heavy metals, and relative freedom from potentially pathogenic bacteria.

Presently, the accepted procedures for preparing poultry manure for recycling as a feedstuff to animals mostly involve a heating-drying step carried out to remove moisture, to lower the bacteria content, and to convert the manure to a solid state suitable for grinding, screening, or pelleting so that the thus-treated poultry manure can be incorporated with other conventional animal feed ingredients, such as forages and/or cereal grains, to form an animal feed ration. See "Recycling Animal Wastes", by R. Blair et al, Feedstuffs, March 5, 1973. It is very difficult to maintain the stability of the manure at a high pH (about 7.0) during the heating step to achieve removal of potentially pathogenic bacteria and to recover a product whose nutrient value is predictable.

SUMMARY OF THE INVENTION

I have discovered a novel process for treating poultry manure to obtain a product which is stable and pathogen-free, and which is suitable as a supplemental feed ingredient in feed rations for animals. The product can be enriched with additives including crude protein equivalent, so as to have an analysis variable within a relatively wide range, as desired to meet particular requirements.

According to the invention, there is provided a process which comprises four critical steps. Steps A and B, described below, can be carried out in optional order, that is, step A followed by step B, or vice versa. Step C is carried out following steps A and B. Step D is carried out after step C. It is preferred to carry out steps A, B, C and D in that order because the acid addition step A confers unexpectedly improved stability on the poultry manure product.

A. To the poultry manure as collected in the poultry raising operation, there is added an amount of acid capable of adjusting the pH of the poultry manure to be less than 7.0, preferably about 5.5 to 6.0. The acid can be added as a liquid or a solid, preferably an aqueous acid solution, and it is added to the manure as soon as is practical following the excretion of the manure. The acid is uniformly mixed in the manure. A portion of the acid reacts with the free ammonia in the manure to form less volatile soluble ammonium salts. The free ammonia otherwise would be released into the atmosphere. It is preferred that the soluble salt formed should be a desirable animal nutrient ingredient in the final product of this process. The remainder of the acid also acts as a catalyst for the polymerization reaction described in the following step C. A mixture of acids can be used, if desired.

The acids that can be used in the process are selected from mineral acids and edible carboxylic acids that are nontoxic and stable under the conditions of use, and that do not impart to the final product either bad taste to animals or supply elements that are unsatisfactory for animal nutrition. The amount of acid added is selected so as to neutralize essentially all of the ammonia in the poultry manure, to change the pH of the poultry manure to less than 7.0, preferably to about 5.5 to 6.0, and the leave present in the thus-treated manure a catalytically effective amount of the acid. It has been found that the addition of from about 0.5 to about 8 weight percent of acid, preferably 1 to 5 weight percent, based in the weight of the poultry manure, calculated as having a zero percent moisture, is effective for this purpose. Suitable acids include phosphoric acid, sulfuric acid, citric acid, acetic acid and propionic acid. It is preferred to use phosphoric acid when it is desired to increase the phosphorus content of the final product. It is also preferred to use sulfuric acid because of its low cost, ready availability and because it supplies sulfur which is a desirable element in animal feed rations. It is especially preferred to use mixtures of phosphoric acid and sulfuric acid.

Some or all of the acid can be replaced by various acidic waste products, such as citrus wastes, apple wastes and grape wastes produced by plants for processing citrus products such as oranges, apples and grapes to produce juices, jellies, jams, sauces and the like. These wastes contain various edible acids which are effective for the same purposes as the acids described above. These wastes also contain other useful organic substances, such as fruit pulp, skin, rind and cores, and various trace elements, which are useful adjuncts in animal feed rations. The wastes are used in amounts capable of supplying acid in the range of acid defined above, when the wastes are used as the sole acid supplying substance. Or they are used in combination with additional acid to supply the required amount of acid to the poultry manure.

B. Formaldehyde or a substance that releases formaldehyde, such as paraformaldehyde, is added to and mixed in the poultry manure, before or after step A, to kill the bacteria present therein. The amount of formaldehyde or formaldehyde-supplying substance added to the poultry manure should be selected to obtain this result. The amount required can be determined by routine experiment on particular sources of poultry manure. It will be advisable to supply an excess of formaldeyde to assure effective results. Generally from about 0.15 to 1.5 weight percent of formaldehyde (calculated as 100 percent formaldehyde), particularly about 0.3 to 0.8 weigt percent, based on te weigt of the poultry manure, calculated as having zero percent moisture, is effective. It has been found, for example, that in most cases the addition of from 1/2 to 2 weight percent of the commercially available 37 percent aqueous solution of formaldehyde (Formalin) to the poultry manure will reduce the bacterial population essentially to zero.

It is preferred to use formaldehyde in the form of commercially available aqueous solutions containing 37 to 44 weight percent of formaldehyde. The commercially available formaldehyde aqueous solutions usually contain an amount of methanol, typically 10 to 15 weight percent of methanol. The methanol does not interfere with the process of the invention. It appears to be a desirable ingredient because it forms an azerotrope with the water in the poultry manure which facilitates rapid drying of the poultry manure as described below.

C. As the third critical step in the process, there is added from about 1 to about 20 weight percent of urea, preferably about 2 to 10 weight percent, based on the weight of poultry manure, calculated as having zero percent moisture. The urea is added in granular form, such as in the form of commerically available urea prills which are of relativlely small particle size. The urea dissolves in the water present in the poultry manure at this time. The mixture is stirred until the urea is dissolved and substantially homogeneous mixture is obtained.

The amount of urea added should be sufficient to react with any residual formaldehyde present in the product following steps A and B. It is preferred to add an excess of urea to assure complete reaction with the residual formaldehyde and to increase the available nitrogen content of the final product to a desired level.

Urea and formaldehyde react in the presence of catalysts such as acids to produce urea-formaldehyde polymers. This technique is employed for making synthetic resins and also in the production of slow-release fertilizers. The reaction produces polymeric chains of various degrees of polymerization.

Thus, the residual formaldehyde in the product of steps A and B reacts with the urea added in step C, in the presence of the residual acid added in step A, to form urea-formaldehyde condensation products. A portion of these condensation products can be stable, and it may pass without change through the digestive system of an animal. Other portions, such as urea-formaldehyde prepolymers and polymers of low degree of polymerization may be digestible by the animal to provide a sustained or prolonged release of crude protein material in the digestive tract of the animal.

The addition of an amount of urea in excess of the amount required to react with the formaldehyde, will establish a level of protein equivalent in the final product of the process of this invention which makes the product inherently more desirable as a feed additive. In addition the added urea is dispersed in the product of steps A and B while it is still somewhat wet, and then it is dried in situ, thus making the material totally homogeneous and offering distinct advantages to purely physical mixing.

The foregoing steps A, B and C can be carried out without preliminary drying of the poultry manure, or partial drying between the steps, if desired. However, improved results can be obtained if the moisture of the poultry manure is controlled and this is a preferred procedure according to the invention. Thus, before the first step (A or B), it is preferred to dry the starting poultry manure (moisture content from 70 to 85 weight percent) to a moisture content of from 50 to 70 weight percent. When step A is carried out first, which is preferred, it is further preferred to dry the product of step A to a moisture content of from 20 to 50 weight percent before step B in order to improve the effectiveness of the bactericidal treatment of step B. It is further preferred to dry the product of the second step of steps A and B, if necessary, to a moisture content of about 15 to 35 weight percent before carrying out step C.

D. The final critical step of the process is drying the product of step C to a condition suitable for storage, packaging and use, generally to a moisture content of less than 15 weight percent, preferably about 10 ± 5 weight percent. This final drying is conducted at a temperature below the melting point of urea, i.e., 132°C.

In sunny and/or arid climates, the steps A, B, C and D can be carried out by placing the starting material poultry manure on concrete slabs so that it is open to the ambient atmosphere. As the poultry manure dries, due to its exposure to the atmosphere, the steps A and B (or B then A), C and D are carried out in sequence therein by continually agitating the poultry manure and adding the chemicals at selected intervals, whereby the entire process is carried out in one installation using only sunlight and air circulation for effecting drying.

Alternatively when ambient conditions do not permit natural drying, then the poultry manure can be dried in low temperature ovens.

It will normally be preferred to allow the mixture of the poultry manure and the chemical to age while undergoing agitation for a period of time allowing each of steps A, B and C to allow the described reactions to proceed to substantially uniform completion throughout the poultry manure and to permit further drying to occur. Aging periods of from 4 to 6 hours between each of the steps is satisfactory, although longer and shorter time periods can be used if circumstances permit.

Various optional steps can follow step D. For example, the product of step D can be screened to remove feathers and non-nutritive debris present therein. This step can be omitted if it is not necessary to remove such impurities from the product. Also, the product can be ground to reduce its particle size if needed. Or the product can be pelletized to obtain a controlled particle size distribution or it can be cubed or compressed in blocks for range feeding for animals.

Additional optional steps that can be employed include the addition of fillers, binders, vitamins, carbohydrates, minerals, coloring agents and odor-masking fragrances to the product of step D. Also, if desired, anhydrous ammonia can be blown through the product of step D to reduce its acidity.

The foregoing steps A, B and C are carried out at ambient temperature. For example in sunny and/or arid climates the entire process can be carried out by placing layers of the poultry manure on covered concrete slabs, adding the chemicals as described above and then in each step agitating the layers to uniformly distribute the chemicals in the poultry manure. Alternatively, mixing can be effected in suitable vessels equipped with mechanical mixing devices.

The product of the process of this invention can be mixed with forages, cereal grains or mixtures thereof to obtain a feed for ruminant animals. It is preferred that the product of this invention comprises from 10 to 30 percent by weight, preferably 15 to 25 percent by weight, based on the total weight of the animal feed.

The invention shall be further described by reference to the following illustrative examples. It will be understood that the invention is not limited to the subject matter of these examples.

EXAMPLE 1

The starting material is fresh chicken manure, with some chicken feathers therein, obtained from a commercial poultry raising farm. The chicken manure is placed in layers on concrete slabs which open to the ambient atmosphere and is air-dried to a moisture content of about 60 weight percent. To 100 pounds of this chicken manure, there is added and mixed 1 pound of phosphoric acid. The mixture is then airdried to a moisture content of about 35 weight percent. There there is added 0.5 pounds of Formalin and the same is uniformly mixed therein. This mixture is then air-dried to a moisture content of 20 to 30 weight percent. Then, 2.0 pounds of urea (prills) is added to and uniformly mixed in the mixture. Then the mixture is subjected to air-drying, while continually agitating the mixture, until the mixture contains about 5 weight percent moisture. The product at this time is a free-flowing powder, containing the chicken feathers therein. The product is then passed through a screen having one-half inch openings to remove the feathers. There is obtained about 45 pounds of final product. The product is essnetially free of pathogenic bacteria. The product has an analysis of protein equivalent (on a dry weight basis) = 49.4 weight percent
phosphorus = 2.34 weight percent

EXAMPLE 2

The procedure of Example 1 is repeated, employing the following addition materials.

| Acid | 0.5 pound phosphoric acid |
| | 0.5 pound sulfuric acid |
| Formalin | 0.5 pound |
| Urea | 6.0 pounds |

The product is essentially bacteria free. It contains a protein equivalent of 71.4 weight percent (on a dry weight basis) and a phosphorus content of 2.1 weight percent.

EXAMPLE 3

The procedure of Example 1 is repeated, employing the following addition materials.

| Acid | 2.0 pounds phosphoric acid |
| Formalin | 0.5 pound |
| Urea | 2.0 pounds |

The product is essentially bacteria free. It contains a protein equivalent of 55.2 weight percent (on a dry weight basis) and a phosphorus content of 3.04 weight percent.

EXAMPLE 4

The procedure of Example 1 is repeated, employing the following additional materials.

| Acid | 1.0 pound phosphoric acid |
| Formalin | 1.0 pound |
| Urea | 4.0 pounds |

The product is essentially bacteria free. It contains a protein equivalent of 63.5 weight percent (on a dry weight basis) and a phosphorus content of 2.26 weight percent.

EXAMPLE 5 (CONTROL)

Fresh poultry waste from the same source is stirred until air dry, without adding other substances to it. The product contains many diverse types of bacteria, and it has a protein equivalent of 32.8 weight percent, on a dry weight basis, and a phosphorus content of 2.02 weight percent.

The embodiments of the invention in which an exclusive property or privilege is claimed are defined as follows:

1. A process for treating poultry manure to transform same to a material suitable for use as a feedstuff for animals, which comprises the steps of:

carrying out the following steps A and B in optional sequence,
- A. mixing poultry manure with an acid to neutralize the ammonia in the poultry manure, to change the pH of the poultry manure to less than 7.0 and to leave present in the poultry manure a catalytically effective amount of the acid, the acid being stable, non-toxic to animals and free of elements that cause bad taste and are unsatisfactory for animal nutrition, the mixing being carried out for a period of time effective to form a substantially uniform homogeneous mixture of said poultry waste and said acid,
- B. mixing into the poultry manure an amount of formaldehyde-supplying substance effective to kill essentially all the pathogenic bacteria present in said poultry waste, the mixing being carried out for a period of time effective to form a substantially uniform homogeneous mixture of the poultry manure, the acid and the formaldehyde-supplying substance,
- C. then mixing into the product from both of steps A and B, granular urea in an amount at least sufficient to react with the residual formaldehyde in the product of step B, to form urea-formaldehyde condensation products therein, and
- D. drying the product of step C to a moisture content of less than about 15 percent.

2. A process according to claim 1, in which in step A the pH of the poultry manure is reduced to from about 5.5 to about 6.0.

3. A process according to claim 1, in which the acid is selected from the group consisting of phosphoric acid, sulfuric acid, citric acid, acetic acid and propionic acid, and the amount of acid is from about 0.5 to about 8.0 weight percent, based on the weight of the poultry manure calculated on a zero percent moisture basis.

4. A process according to claim 1, in which said acid is phosphoric acid, sulfuric acid or mixture of phosphoric acid and sulfuric acid, and the amount of acid is from about 1 to about 5 weight percent, based on the weight of poultry manure calculated on a zero percent moisture basis.

5. A process according to claim 1, in which the formaldehyde-supplying substance is added in an amount of from about 0.15 to 1.5 weight percent, based on the weight of poultry manure calculated on a zero percent moisture basis.

6. A process according to claim 4, in which the formaldehyde-supplying substance is an aqueous solution of formaldehyde, and the amount thereof is from about 0.3 to 0.8 weight percent of formaldehyde calculated as 100 percent formaldehyde, based on the weight of poultry manure calculated on a zero percent moisture basis.

7. A process according to claim 1, in which the amount of urea added is from about 1 to about 20 weight percent, based on the weight of poultry manure calculated on a zero percent moisture basis.

8. A process according to claim 6, in which the amount of urea added is from about 2 to about 10 weight percent, based on the weight of poultry manure calculated on a zero percent moisture basis.

9. A process according to claim 1, in which step A is carried out first and step B is carried out second, and in which before step A the poultry manure is dried to a moisture content of from about 50 to about 70 weight percent, and in which before step B the product of step A is dried to a moisture content of from about 20 to about 50 weight percent, and in which before step C the moisture content of the product of step B is regulated to be from about 15 to about 35 weight percent.

10. A process according to claim 1, in which in step D the product of step C is dried at a temperature below 132°C.

11. A process according to claim 1, in which an acid-containing substance selected from the group consisting of citrus wastes, apple waste and grape waste is employed to supply some or all of the acid added in step A.

12. An animal feed comprising a mixture of the product of claim 1 and forage, cereal grains or mixtures thereof.

13. A method of feeding a ruminant animal which comprises feeding to said animal an animal feed as claimed in claim 12.

* * * * *